(12) United States Patent
Takagi

(10) Patent No.: US 9,182,391 B2
(45) Date of Patent: Nov. 10, 2015

(54) METHOD OF PRODUCING INSOLUBLE CARRIER PARTICLES, INSOLUBLE CARRIER PARTICLES, MEASUREMENT REAGENT, SPECIMEN ANALYZING TOOL, AND IMMUNOTURBIDIMETRIC ASSAY

(75) Inventor: Hidenori Takagi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1222 days.

(21) Appl. No.: 12/936,783

(22) PCT Filed: Apr. 21, 2009

(86) PCT No.: PCT/JP2009/057903
§ 371 (c)(1),
(2), (4) Date: Oct. 7, 2010

(87) PCT Pub. No.: WO2009/136541
PCT Pub. Date: Nov. 12, 2009

(65) Prior Publication Data
US 2011/0027915 A1    Feb. 3, 2011

(30) Foreign Application Priority Data

May 9, 2008 (JP) ................................ 2008-123971

(51) Int. Cl.
*G01N 33/543* (2006.01)
(52) U.S. Cl.
CPC .... *G01N 33/54353* (2013.01); *G01N 33/54313* (2013.01)
(58) Field of Classification Search
None
See application file for complete search history.

(56) References Cited

U.S. PATENT DOCUMENTS

| | | | | |
|---|---|---|---|---|
| 4,066,744 | A * | 1/1978 | Price et al. | 435/7.36 |
| 6,548,310 | B1 * | 4/2003 | Murata et al. | 436/518 |
| 6,767,635 | B1 * | 7/2004 | Bahr et al. | 428/402 |
| 2003/0207253 | A1 * | 11/2003 | Kaylor et al. | 435/5 |
| 2004/0091940 | A1 | 5/2004 | Sawai et al. | |
| 2005/0069967 | A1 | 3/2005 | Sumida et al. | |
| 2005/0186146 | A1 * | 8/2005 | Gong et al. | 424/46 |
| 2007/0172653 | A1 * | 7/2007 | Berkland et al. | 428/402 |
| 2008/0171090 | A1 * | 7/2008 | Yagi et al. | 424/490 |
| 2009/0035264 | A1 * | 2/2009 | Hastedt et al. | 424/85.2 |
| 2009/0176084 | A1 * | 7/2009 | Yoshihara et al. | 428/313.3 |

FOREIGN PATENT DOCUMENTS

| | | | | |
|---|---|---|---|---|
| EP | 1 385 001 | | 1/2004 | G01N 33/543 |
| EP | 1 416 277 | | 5/2004 | G01N 33/545 |
| JP | 61-97568 | | 5/1986 | |
| JP | 61097568 | * | 5/1986 | G01N 33/54 |
| JP | 63-228069 | | 9/1988 | |
| JP | 5-99924 | A | 4/1993 | |
| JP | H5-99924 | A | 4/1993 | |
| JP | 11-258239 | | 9/1999 | |
| JP | 2004-117022 | | 4/2004 | |
| JP | 2004-117068 | | 4/2004 | |
| JP | 2005-106609 | | 4/2005 | |
| WO | WO 02/079782 | | 10/2002 | |
| WO | WO 2009/104369 | | 8/2009 | G01N 33/543 |

OTHER PUBLICATIONS

Extended European Search Report dated Apr. 5, 2011 in corresponding European Patent Application No. EP 0974266.2.
Office Action issued in corresponding European Patent Application No. 09742666.2 dated Feb. 11, 2014.

* cited by examiner

*Primary Examiner* — Ann Lam
(74) *Attorney, Agent, or Firm* — Morgan, Lewis & Bockius LLP

(57) ABSTRACT

The present invention provides a measurement reagent that is capable of suppressing nonspecific aggregation even when the amount of antibody to be carried is increased, and is capable of measuring in a wide measurement concentration range with high measurement sensitivity; an immunoturbidimetric assay using the same; and a method of producing thereof. A method of producing an insoluble carrier particle of the present invention is a method of producing an insoluble carrier particle carrying an antibody or an antigen on a particle surface thereof. The method includes a sensitization reaction processes in which the antibody or the antigen is brought into contact with the insoluble carrier particle in the presence of an amino acid with a charged polar side chain in a sensitization reaction solution. The insoluble carrier particles obtained by the producing method of the present invention show favorable dispersibility because nonspecific aggregation is suppressed. As can be seen from Examples 1-1 to 1-4 in FIG. 3, when the insoluble carrier particles are applied to measurement by an immunoturbidimetric assay, a wide measurement concentration range and high measurement sensitivity can be achieved.

19 Claims, 4 Drawing Sheets

METHOD OF PRODUCING INSOLUBLE CARRIER PARTICLES, INSOLUBLE CARRIER PARTICLES, MEASUREMENT REAGENT, SPECIMEN ANALYZING TOOL, AND IMMUNOTURBIDIMETRIC ASSAY

TECHNICAL FIELD

The present invention relates to a method of producing insoluble carrier particles, insoluble carrier particles, a measurement reagent, a specimen analyzing tool, and an immunoturbidimetric assay.

BACKGROUND ART

Heretofore, as immunological assays, enzyme immunoassays (EIA), immunoturbidimetric assays, and the like have been used. Among them, in recent years, immunoturbidimetric assays using insoluble carrier particles have been used widely in laboratory tests and the like because they are applicable to autoanalyzers.

The immunoturbidimetric assays usually use insoluble carrier particles carrying antigens or antibodies, which are measurement objects. When samples contain measurement objects, the measurement objects are bound to the antigens or antibodies carried by the insoluble carrier particles, and the insoluble carrier particles thereby are aggregated. Therefore, measurement objects can be detected by measuring the level of the aggregation.

In laboratory tests, disorders are diagnosed by measuring, for example, concentrations of antigens or antibodies contained in biological samples as diagnostic indices by the immunoturbidimetric assay. Since concentrations of antigens or antibodies contained in biological samples differ greatly depending on the presence or absence of disorders, for example, the inspection methods are required to be measurable over a wider range concentration.

Immunoturbidimetric assays using insoluble carrier particles can, from their measurement principles, widen the measurement concentration ranges of measurement objects by raising the upper limit of the amount of antibody or antigen that is reactable. To achieve this, insoluble carrier particles are required to have larger amount of antibody or antigen. However, with respect to insoluble carrier particles used in immunoturbidimetric assays, usually, when the insoluble carrier particles carry antibodies or antigens at functional groups on the surfaces of the particles, the electric charges of the surfaces thereof are decreased. This causes problems in which aggregation reactions of particles themselves and aggregation reactions (nonspecific aggregation) by substances other than antibodies or antigens occur easily, dispersibility is decreased, and measurement sensitivity is decreased.

Hence, with respect to the immunoturbidimetric assays, with the aim of suppressing nonspecific aggregation, a method of using proteins non-specific to antigens (Patent document 1), a method of using surfactants (Patent document 2), and a method of using salts (Patent document 3) have been developed. However, in the method of using proteins non-specific to antigens, when the amount of antibody or antigen to be sensitized with insoluble carrier particles is increased, the efficiency of suppressing nonspecific aggregation is decreased. Further, in the method of using surfactants, there is the possibility of losing reactivity because antibodies or antigens physically adsorbed are removed or denatured. Moreover, in the method of using salts, there is the possibility of decreasing reactivity and sensitivity of antibodies or antigens. According to these methods, the quality of insoluble carrier particles tends to vary depending on the type, lot, and the like of antibodies or antigens to be carried.

Patent document 1: JP 2004-117068A
Patent document 2: JP 11(1999)-258239A
Patent document 3: JP 2004-117022A

DISCLOSURE OF INVENTION

Problem to be Solved by the Invention

Therefore, an object of the present invention is to provide a method of producing insoluble carrier particles, insoluble carrier particles, a measurement reagent, a specimen analyzing tool, and an immunoturbidimetric assay capable of suppressing nonspecific aggregation even when the amount of antibody or antigen to be carried is increased.

Means for Solving Problem

In order to achieve the aforementioned object, a method of producing an insoluble carrier particle of the present invention is a method of producing an insoluble carrier particle carrying an antibody or an antigen on a particle surface thereof. The method includes at least one of the following sensitization reaction processes (A) and (B):

(A) bringing the antibody or the antigen into contact with the insoluble carrier particle in the presence of an amino acid with a charged polar side chain in a sensitization reaction solution, wherein a concentration of the amino acid with a charged polar side chain in the sensitization reaction solution is more than 0.1 mol/L and is equal to or less than 1 mol/L; and (B) bringing the antibody or the antigen into contact with the insoluble carrier particle in the presence of an amino acid with a charged polar side chain in a sensitization reaction solution, wherein a latex particle for chemical bonding is used as the insoluble carrier particle.

An insoluble carrier particle of the present invention is an insoluble carrier particle used in an immunoturbidimetric assay. The insoluble carrier particle is produced by the method of producing an insoluble carrier particle according to the present invention.

A measurement reagent of the present invention is a measurement reagent used in an immunoturbidimetric assay. The measurement reagent contains the insoluble carrier particle according to the present invention.

A specimen analyzing tool of the present invention is a specimen analyzing tool containing the measurement reagent according to the present invention.

An immunoturbidimetric assay of the present invention is an immunoturbidimetric assay including:
an aggregation reaction process immunoreacting insoluble carrier particles carrying antibodies or antigens on particle surfaces thereof with measurement objects, which are antigens or an antibodies, to aggregate the insoluble carrier particles in an immunoreaction solution; and
a measurement process measuring change in turbidity of the immunoreaction solution due to the aggregation reaction. The insoluble carrier particles according to the present invention are used as the insoluble carrier particles.

Effects of the Invention

The method of producing an insoluble carrier particle of the present invention can produce insoluble carrier particles with suppressed nonspecific aggregation even when the amount of antibody or antigen carried by the insoluble carrier particles is increased. Further, the method of producing of the present invention is less affected by the type of antibody or antigen and the difference between the lot of antibody or antigen. Moreover, the method of producing of the present invention is applicable as long as a sensitization reaction is performed in the presence of an amino acid with a charged polar side chain, and the process thereof is simple. Since the nonspecific aggregation of the insoluble carrier particles of the present invention due to increase in the amount of antibody or antigen is suppressed, the insoluble carrier particles of the present invention can carry a sufficient amount of antibody or antigen. Therefore, when the insoluble carrier particles of the present invention are applied to an immunoturbidimetric assay, a wide measurement concentration range and high measurement sensitivity can be achieved. Further, since the amino acid with a charged polar side chain is bound to the insoluble carrier particles, the insoluble carrier particles of the present invention are less affected by concentration due to drying, for example, and are applicable to specimen analyzing tools such as a test piece that is a dry reagent for immunoassay and a microchip. Therefore the insoluble carrier particles of the present invention are applicable to small-sized autoanalyzers.

The mechanism of suppressing the nonspecific aggregation with respect to the insoluble carrier particles of the present invention can be estimated as follows, for example. That is, when the insoluble carrier particles are sensitized with the antibodies, the antibodies physically adsorb to the surfaces of the insoluble carrier particles, and then bind to functional groups (for example, a carboxyl group) on the surfaces of the insoluble carrier particles in vicinity. Therefore, electric charges of the surfaces of the insoluble carrier particles are decreased. On the other hand, because of the steric hindrance due to the bound antibodies, some of the functional groups on the surfaces remain without being bound with the antibodies. During the sensitization reaction, antibodies or antigens are brought into contact with the insoluble carrier particles in the presence of the amino acid with a charged polar side chain. Then, the amino acid with a charged polar side chain of high hydration binds to the insoluble carrier particles, and further, the amino acid with a charged polar side chain binds to water molecules. Therefore, the hydrophilicity and the electric charge are increased to improve the dispersibility of the insoluble carrier particles. As a result, the nonspecific aggregation is suppressed. However, the mechanism is only an estimation and the present invention is neither specified nor limited by the aforementioned estimation.

DESCRIPTION OF THE INVENTION

Figure 1:
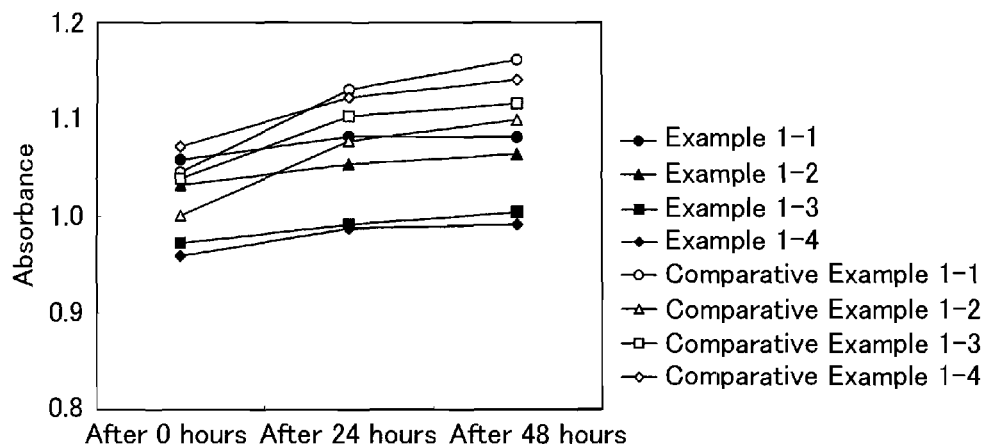
FIG. 1 is a graph showing measurement results of the dispersibility with respect to Example of the present invention and Comparative Example.

With respect to the method of producing an insoluble carrier particle of the present invention, the amino acid with a charged polar side chain is preferably a basic amino acid or an acidic amino acid.

With respect to the method of producing an insoluble carrier particle of the present invention, in the sensitization reaction process (A), the insoluble carrier particle is preferably a latex particle.

With respect to the method of producing an insoluble carrier particle of the present invention, in the sensitization reaction process (A), the latex particle is preferably a latex particle for chemical bonding.

Preferably, the measurement reagent of the present invention contains an insoluble carrier particle group including a plurality of insoluble carrier particles, the insoluble carrier particle group includes two types of insoluble carrier particle groups having different average particle sizes, and at least one of the two types of insoluble carrier particle groups is an insoluble carrier particle group including a plurality of insoluble carrier particles according to the present invention.

With respect to the measurement reagent of the present invention, an insoluble carrier particle group having a larger average particle size out of the two types of insoluble carrier particle groups is preferably an insoluble carrier particle group including a plurality of insoluble carrier particles according to the present invention.

In the measurement reagent of the present invention, for example, the average particle size of the insoluble carrier particle according to the present invention is preferably in the range of 0.03 to 2.0 μm, more preferably in the range of 0.08 to 2.0 μm, and further preferably in the range of 0.12 to 0.5 μm.

The specimen analyzing tool of the present invention may be any one of a test piece, a cartridge, and a microchip.

Preferably, with respect to the immunoturbidimetric assay of the present invention, in the aggregation reaction process, an insoluble carrier particle group including a plurality of insoluble carrier particles is used. The insoluble carrier particle group includes two types of insoluble carrier particle groups having different average particle sizes, and at least one of the two types of insoluble carrier particle groups is an insoluble carrier particle group including a plurality of insoluble carrier particles according to the present invention.

With respect to the immunoturbidimetric assay of the present invention, an insoluble carrier particle group having a larger average particle size out of the two types of insoluble carrier particle groups is preferably an insoluble carrier particle group including a plurality of insoluble carrier particles according to the present invention.

In the immunoturbidimetric assay of the present invention, for example, the average particle size of the insoluble carrier particle according to the present invention is preferably in the range of 0.03 to 2.0 µm, more preferably in the range of 0.08 to 2.0 µm, and further preferably in the range of 0.12 to 0.5 µm.

Next, the present invention is explained with examples.

<Producing Method>

As described above, the producing method of the present invention is a method of producing insoluble carrier particles carrying antibodies or antigens on the particle surfaces thereof. The method includes a sensitization reaction process in which the antibodies or the antigens are brought into contact with the insoluble carrier particles in the presence of an amino acid with a charged polar side chain in a sensitization reaction solution.

As described above, the producing method of the present invention includes at least one of the following sensitization reaction processes (A) and (B) as the sensitization reaction process. Hereinafter, in the producing method of the present invention, a producing method including the following sensitization reaction process (A) is referred to as a "producing method A" and a producing method including the following sensitization reaction process (B) is referred to as a "producing method B".

(A) bringing the antibodies or the antigens into contact with the insoluble carrier particles in the presence of an amino acid with a charged polar side chain in a sensitization reaction solution, wherein the concentration of the amino acid with a charged polar side chain in the sensitization reaction solution is more than 0.1 mol/L and is equal to or less than 1 mol/L; and (B) bringing the antibodies or the antigens into contact with the insoluble carrier particles in the presence of an amino acid with a charged polar side chain in a sensitization reaction solution, wherein a latex particle for chemical bonding is used as the insoluble carrier particle.

In the producing method of the present invention, the sensitization reaction solution contains the insoluble carrier particles carrying antibodies or antigens and the amino acid with a charged polar side chain.

In the present invention, the amino acid with a charged polar side chain is an amino acid having a polar and a charged side chain. Therefore, the amino acid with a charged polar side chain is hydrophilic and is positively charged or negatively charged in a solution. With respect to the amino acid with a charged polar side chain, an amino acid that is positively charged is a basic amino acid and an amino acid that is negatively charged is an acidic amino acid. Examples of the basic amino acid include arginine, histidine, and lysine. Examples of the acidic amino acid include an aspartic acid and a glutamic acid. The amino acid with a charged polar side chain is applicable as long as it is positively charged or negatively charged in a solution. For example, the amino acid with a charged polar side chain includes salts of the amino acid with a charged polar side chain. The salts are not particularly limited. Examples thereof include sodium salt and potassium salt, and a specific example thereof includes acidic amino acid salt such as sodium aspartate. Further, an example of the salts includes hydrochloride, and a specific example thereof includes basic amino acid salt such as arginine hydrochloride and lysine hydrochloride. Above all, as the amino acid with a charged polar side chain used in the producing method of the present invention, sodium aspartate and sodium glutamate are preferable.

In the producing method A of the present invention, the concentration of the amino acid with a charged polar side chain in the sensitization reaction solution is more than 0.1 mol/L and is equal to or less than 1 mol/L as described above, and is preferably in the range of 0.2 mol/L to 0.8 mol/L.

In the producing method B of the present invention, the concentration of the amino acid with a charged polar side chain in the sensitization reaction solution may be, for example, more than 0.1 mol/L and may be equal to or less than 1 mol/L, and is preferably in the range of 0.2 mol/L to 0.8 mol/L, although it is not particularly limited.

In the producing method A of the present invention, the insoluble carrier particle is not particularly limited, and examples thereof include synthetic polymer particles, inorganic compound particles, and polysaccharide particles. The synthetic polymer particle is not particularly limited, and examples thereof include latex particles and polylactic acid particles, and latex particles are preferable. The material of the latex particle is not particularly limited, and examples thereof include polystyrene, styrene-butadiene copolymer, styrene-acrylate copolymer, styrene-maleic acid copolymer, polyethylenimine, polyacrylic acid, polymethacrylic acid, and polymethylmethacrylate, and polystyrene is preferable. The inorganic compound particle is not particularly limited, and examples thereof include porous glass particles and silica particles. The polysaccharide particle is not particularly limited, and examples thereof include agarose particles, dextran particles, and chitosan particles.

In the producing method A of the present invention, the insoluble carrier particle may be insoluble carrier particles for chemical bonding or insoluble carrier particles for physical adsorption. The insoluble carrier particle for chemical bonding is not particularly limited, and insoluble carrier particles with functional groups on the particle surfaces thereof can be used.

The functional group is not particularly limited, and examples thereof include a carboxyl group, an amino group, a sulfo group, a carbinol group, a carbamoyl group, a trimethylamino group, a polyethylenimine group, a phenolic hydroxyl group, an alcoholic hydroxyl group such as carbinol group, a polyethyleneglycol group, a polyethylene glycol group having a terminal carboxyl group, a polyethylene glycol group having a terminal carboxyl group, an octyl group, an octadecyl group, and a trimethylsilyl group, and a carboxyl group is preferable.

Similar to the producing method B, in the producing method A of the present invention, the insoluble carrier particle may be the latex particle for chemical bonding described later.

In the producing method B of the present invention, the aforementioned latex particles for chemical bonding are used as the insoluble carrier particle. As the latex particles for chemical bonding, latex particles with functional groups on the particle surfaces thereof can be used. The material of the latex particle is not particularly limited, and examples thereof include the same materials as those described above. Among them, polystyrene, styrene-butadiene copolymer, styrene-acrylate copolymer are preferable, and polystyrene is more preferable. The functional group is not particularly limited, and examples thereof include the same functional groups as those described above. Among them, a carboxyl group, an amino group, a sulfo group, a carbinol group, and an acylamino group are preferable, and a carboxyl group is more preferable.

In the producing method of the present invention, the average particle size of the insoluble carrier particle is not particularly limited, and is, for example, in the range of 0.03 µm to 2.0 µm, preferably in the range of 0.05 µm to 1.0 µm, and further preferably in the range of 0.07 µm to 0.5 µm.

In the producing method of the present invention, the concentration of the insoluble carrier particle in the sensitization reaction solution is not particularly limited, and is, for example, in the range of 0.1 w/v % to 10 w/v %, preferably in the range of 0.3 w/v % to 8 w/v %, and more preferably in the range of 0.5 w/v % to 5 w/v %.

In the present invention, the antigens carried by the insoluble carrier particles are not particularly limited, and can be determined suitably according to the objects to be analyzed. Specific examples thereof include CRP (C-reactive protein), ASO (antistreptolysin O), AFP (α-fetoprotein), FDP (fibrin degradation product), CEA (carcinoembryonic antigen), HCGβ (human chorionic gonadotropin-β), SCC (squamous cell carcinoma-related antigen), a rheumatoid factor, HbAlc, creatinine, fibrinogen, various viruses (hepatitis virus, HTLV-1, HIV, HCV, HBs, HBe) antigens, and various enzymes.

In the present invention, the antibodies carried by the insoluble carrier particles are not particularly limited, and can be determined suitably according to objects to be analyzed. The type of the antibody is not particularly limited, and examples thereof include immunoglobulin molecules such as IgG, IgA, IgM, IgD, and IgE and antibody fragments such as Fab, Fab', F (ab')$_2$. The antibodies may be prepared from serums derived from mice, rabbits, goats, sheep, and chickens by conventionally known methods, or commercially available various antibodies may be used, and it is not particularly limited. The antibodies are not particularly limited, and specific examples thereof include the antibodies for the aforementioned various antigens.

The antibodies carried by the insoluble carrier particles may be polyclonal antibodies or monoclonal antibodies. In the sensitization reaction process, the both antibodies may be carried by the insoluble carrier particles or one of the antibodies may be carried by the insoluble carrier particles.

In the producing method of the present invention, the concentration of the antibody in the sensitization reaction solution is not particularly limited, and is, for example, in the range of 0.01 mg/mL to 20 mg/mL, preferably in the range of 0.05 mg/mL to 10 mg/mL, and further preferably in the range of 0.1 mg/mL to 5 mg/mL. Further, in the case where both the polyclonal antibodies and the monoclonal antibodies are sensitized with the insoluble carrier particles, the concentration ratio between the polyclonal antibody and the monoclonal antibody (polyclonal antibody:monoclonal antibody) is not particularly limited, and is, for example, in the range of 1:9 to 7:3, and preferably in the range of 1:9 to 5:5. In this state, the ratio between the polyclonal antibody and the monoclonal antibody in the sensitization reaction solution may be a ratio by weight or a ratio of the number of antibody molecules.

In the producing method of the present invention, the sensitization reaction solution contains the amino acid with a charged polar side chain, the antibodies or the antigens, and the insoluble carrier particles. In addition, the sensitization reaction solution may contain other components. The other components are not particularly limited, and examples thereof include a buffer solution and bovine serum albumin (BSA).

The buffer solution is not particularly limited, and an MES (2-(N-Morpholino)ethanesulfonic acid) buffer solution, a phosphate buffer solution, and a Tris (tris(hydroxymethyl)aminomethane) buffer solution can be used, for example. The pH of the buffer solution is, for example in the range of 5 to 9, and preferably in the range of 6.0 to 7.5.

In the producing method of the present invention, the sensitization reaction process is not particularly limited, and can be performed suitably by the conventionally known methods such as a chemical bonding method.

The producing method of the present invention is not particularly limited as long as it includes the sensitization reaction process. For example, the producing method further may include a functional group activation process, a washing process, and a blocking process.

For example, the functional group activation process is a process for activating the functional groups, such as an amino group and a carboxyl group, on the surfaces of the insoluble carrier particles in advance of the sensitization reaction process. The functional group activation process is not particularly limited. For example, the insoluble carrier particles may react in a buffer solution containing NHS (N-hydroxysuccinimide) and EDAC (1-Ethyl-3-(3-dimethylaminopropyl)carbodiimide). The functional groups are not particularly limited, and examples thereof include the aforementioned functional groups.

For example, the washing process is a process for washing the insoluble carrier particles with a buffer solution or the like. The washing process is preferably performed after the sensitization reaction process, for example. The washing process is not particularly limited and can be performed by a conventionally known method. The buffer solution is not particularly limited, and examples thereof include the aforementioned MES buffer solution, phosphate buffer solution, and Tris buffer solution.

The blocking process is preferably performed after the washing process, for example. For example, the blocking process is a process for covering the surfaces of the insoluble carrier particles with BSA or the like in order to suppress nonspecific binding of antigens or antibodies that are measurement objects. For example, the blocking process can be performed suitably by the conventionally known methods, and the insoluble carrier particles may be left to stand overnight in a buffer solution containing a blocking agent, for example. The blocking agent is not particularly limited, and examples thereof include BSA. The buffer solution is not particularly limited, and examples thereof include the aforementioned buffer solutions.

<Insoluble Carrier Particle>

As described above, the insoluble carrier particles of the present invention are insoluble carrier particles used in immunoturbidimetric assays and are produced by the producing method of the present invention. The insoluble carrier particles of the present invention are not particularly limited as long as they are produced by the producing method of the present invention. In the present invention, examples of insoluble carrier particles carrying antibodies or antigens, and antibodies or antigens carried by the insoluble carrier particles are the same as those described above.

With respect to the insoluble carrier particles produced by the producing method of the present invention, the amino acid with a charged polar side chain is bound to the particle surfaces thereof, for example. The method of binding is not particularly limited and the amino acid with a charged polar side chain may be bound directly to the insoluble carrier particles as described above, or may be bound to the insoluble carrier particles indirectly. In the latter case, the residues of the amino acid with a charged polar side chain may be bound to functional groups chemically bound to the surfaces of the insoluble carrier particles.

<Measurement Reagent>

As described above, the measurement reagent of the present invention contains the insoluble carrier particles of the present invention. In the measurement reagent of the present invention, the insoluble carrier particles of the present invention may be insoluble carrier particles produced by one of the producing methods A and B of the present invention, or may be a combination of the insoluble carrier particles produced by the aforementioned producing methods.

The measurement reagent of the present invention may contain an insoluble carrier particle group, for example. In the present invention, the insoluble carrier particle group is an insoluble carrier particle group including plural insoluble carrier particles described above having certain performances and forms. The insoluble carrier particle group may include, for example, one type of insoluble carrier particle group or plural types of insoluble carrier particle groups, and it is not particularly limited. In the former case, the insoluble carrier particle group is an insoluble carrier particle group including plural insoluble carrier particles of the present invention. Further, in the latter case, the insoluble carrier particle group may include one type of or two or more types of insoluble carrier particle groups including plural insoluble carrier particles of the present invention, for example.

Preferably, the insoluble carrier particle group includes two or more types of insoluble carrier particle groups having different average particle sizes, and out of these, at least one of the insoluble carrier particle groups is an insoluble carrier particle group including plural insoluble carrier particles of the present invention, for example, although it is not particularly limited. In the case where the insoluble carrier particle group includes two or more types of insoluble carrier particle groups having different average particle sizes, although it is not particularly limited, the insoluble carrier particle group including plural insoluble carrier particles of the present invention may be an insoluble carrier particle group having the largest average particle size out of the insoluble carrier particle groups having different average particle sizes. When the measurement reagent of the present invention contains two or more types of insoluble carrier particles having different average particle sizes, measurement can be performed in the wider concentration range, and sufficiently high measurement accuracy can be obtained. The type of the average particle size is not particularly limited, and examples thereof include an average number size, an average length size, an average body area size, an average mass size, an average volume size, an average surface area size, an equivalent specific surface size, a median size, and a mode size.

In the present invention, "an insoluble carrier particle group includes two or more types of insoluble carrier particle groups having different average particle sizes" may mean, for example, that the insoluble carrier particle group includes two or more types of insoluble carrier particle groups showing different average particle sizes when average particle sizes are measured by conventionally known predetermined methods; or that a histogram shows two or more peaks when the particle size distribution of the whole insoluble carrier particles to be used is measured. In the latter case, in the present invention, for example, "an insoluble carrier particle group including two or more types of insoluble carrier particle groups having different average particle sizes" also can be described as "an insoluble carrier particle group including two or more peaks in its particle size distribution". Examples of a method of measuring the particle size distribution include microscopy using an optical microscope and an electron microscope, a light scattering method, a light blocking method, laser diffractometry, an electric resistance method, an electrozone sensing method, a screening method, a liquid phase precipitation method, a centrifugal precipitation method, and an inertial impaction method. The average particle size can be calculated also from a particle size distribution obtained by the aforementioned methods. In the present invention, the two or more types of insoluble carrier particle groups having different average particle sizes may be two or more types of insoluble carrier particle groups that can be classified with two or more types of screens having different mesh sizes.

Two or more types of insoluble carrier particle groups having different average particle sizes included in the insoluble carrier particle group each may include particles with the average particle size of ±15%, and preferably include particles with the average particle size of ±5%, with reference to each average particle size.

The type of the insoluble carrier particle groups having different average particle sizes is not particularly limited as long as it is more than one. For example, the insoluble carrier particle groups may be two to five types, preferably two to three types, and more preferably two types.

For example, in the case where the insoluble carrier particle group includes two insoluble carrier particle groups having different average particle sizes, the average particle size of the insoluble carrier particle having the larger average particle size (hereinafter, referred to as "larger particle") is not particular limited, and is, for example in the range of 0.08 μm to 2.0 μm, preferably in the range of 0.1 μm to 1.0 μm, and more preferably in the range of 0.12 μm to 0.5 μm. Further, in this case, the average particle size of the insoluble carrier particle having smaller average particle size (hereinafter, referred to as "smaller particle") also is not particular limited, and is, for example in the range of 0.03 μm to 0.2 μm, preferably in the range of 0.05 μm to 0.15 μm, and more preferably in the range of 0.07 μm to 0.12 μm.

In the case where the insoluble carrier particle group includes two insoluble carrier particle groups having different average particle sizes, for example, polyclonal antibodies and monoclonal antibodies are preferably supported on at least one of the larger particles and the smaller particles, although it is not limited. The measurement reagent carrying antibodies in this manner can measure measurement objects having concentrations from lower degree to higher degree with high sensitivity by use of the small amount of particle and antibody, and can set dilution rates of specimens at low degrees, for example.

The concentration of the insoluble carrier particle in the measurement reagent of the present invention is not particularly limited, and is, for example, in the range of 0.011 w/v % to 15 w/v %, preferably in the range of 0.06 w/v % to 6 w/v %, and more preferably in the range of 0.15 w/v % to 1.5 w/v %.

In the case where the measurement reagent of the present invention contains two types of insoluble carrier particle groups having different average particle sizes, for example, the concentration of the larger particle in the measurement reagent is, for example. in the range of 0.001 w/v % to 5 w/v %, preferably in the range of 0.01 w/v % to 1 w/v %, and more preferably in the range of 0.05 w/v % to 0.5 w/v %.

In the case where the measurement reagent of the present invention contains two types of insoluble carrier particle groups having different average particle sizes, for example, the concentration of the group of smaller particles in the measurement reagent is, for example, in the range of 0.01 w/v % to 10 w/v %, preferably in the range of 0.05 w/v % to 5 w/v %, and more preferably in the range of 0.1 w/v % to 1 w/v %.

The measurement reagent of the present invention may contain a buffer solution, sugar, protein, glycoside, a high molecular compound, an preservative, and the like as components other than the insoluble carrier particles. The buffer solution is not particularly limited, and examples thereof include the aforementioned MES buffer solution, phosphate buffer solution, and Tris buffer solution. The sugar is not particularly limited, and examples thereof include sucrose, maltose, and glucose. The protein is not particularly limited, and examples thereof include bovine serum albumin (BSA) and gelatin. The glycoside is not particularly limited, and examples thereof include saponin and digitonin. The high molecular compound is not particularly limited, and examples thereof include polyethyleneglycol and polyvinylpyrrolidone. The preservative is not particularly limited, and examples thereof include sodium azide and Kathon®.

<Specimen Analyzing Tool>

As described above, the specimen analyzing tool of the present invention contains the measurement reagent of the present invention. The specimen analyzing tool is applicable as long as it contains the measurement reagent of the present invention, and structures and conditions other than this are not limited at all. In the specimen analyzing tool of the present invention, for example, according to the configuration thereof, the measurement reagent may be placed in a dried state or in a liquid state such as dispersion liquid or suspension.

The configuration of the specimen analyzing tool is not limited at all, and examples thereof include a cartridge, a test piece, and a microchip. Preferably, these specimen analyzing tools are connectable to general-purpose measuring instruments for detecting the aggregation level due to an antigen-antibody reaction, for example.

The cartridge is not particularly limited. For example, the cartridge has a configuration in which a substrate is provided with a reagent bath in which the measurement reagent is placed. Examples of the cartridge include the one provided with a storing bath (reagent bath) filled with the reagent for immunoreaction and a reaction bath performing immunoreaction, and to be incorporated into an autoanalyzer to measure components contained in specimens; and the like. In this case, the storing bath (reagent bath) may be filled with the measurement reagent of the present invention or the reaction bath may be filled with the measurement reagent of the present invention, and it is not particularly limited. With respect to the cartridge, for example, before or after being connected to the measuring instrument, a measurement sample is introduced into the reagent bath in which the measurement reagent is placed, and the aggregation level in the reagent bath is measured with the measuring instrument after an antigen-antibody reaction. Further, with respect to the cartridge, the substrate further may be provided with a reaction bath that is in communication with the reagent bath via a flow passage. In this case, the measurement sample is introduced into the reagent bath, the mixture of the measurement sample and the measurement reagent is transferred to the reaction bath via the flow passage, and the aggregation level in the reaction bath may be measured. The cartridge can measure the component contained in the specimen or the concentration thereof from the aggregation level. The measurement reagent of the present invention to be placed in the reagent bath of the cartridge may be in a liquid state (dispersion liquid) or a dried state.

The test piece may have a configuration in which a reagent portion containing the measurement reagent of the present invention is placed on a substrate being a reed shape or the like. Examples of the material of the reagent portion include a filter paper and various polymeric porous bodies. With respect to such a test piece, the measurement sample is added to the reagent portion in which the measurement reagent is placed, and the aggregation level in the reagent portion is measured with the measuring instrument after an antigen-antibody reaction. Examples of the test piece include the one provided with a reagent layer containing the measurement reagent (reagent for immunoreaction) and a reagent for detection on a support having a reed shape; and the like. With respect to such a test piece, for example, the measurement sample is added to the reagent layer containing the insoluble carrier particles of the present invention, and the aggregation level in the reagent portion is measured with the reagent for detection after an antigen-antibody reaction. The composition of the reagent for detection is not particularly limited, and examples thereof include a coloring dye, a fluorescent dye, and a buffer solution. In the test piece, the measurement reagent of the present invention is preferably placed in a dried state, for example. For example, before or after placing the porous body or the like to the substrate, the measurement reagent in the state of dispersion liquid is supplied to the porous body or the like, and then dried.

A chip such as the microchip may have a configuration in which a substrate is provided with an inlet for samples, a reagent portion, and a flow passage, and the inlet and the reagent portion are in communication with each other via the flow passage. With respect to such a chip, for example, the measurement sample is introduced from the inlet, the measurement sample is transferred to the reagent portion via the flow passage, and an antigen-antibody reaction is performed in the reagent portion. After the antigen-antibody reaction, the aggregation level in the reagent portion is measured with the measuring instrument. The measurement reagent of the present invention to be placed to the reagent portion of the chip may be in a liquid state or a dried state. The chip such as the microchip may be the one provided with flow passages for introducing and separating samples and a reagent bath. With respect to such a chip, the flow passage for separation may contain the insoluble carrier particles of the present invention.

Further, with respect to these specimen analyzing tools, for example, the reagent portions and the reagent bathes further may contain reagents for detecting aggregates as required.

<Immunoturbidimetric Assay>

As described above, the immunoturbidimetric assay of the present invention includes an aggregation reaction process immunoreacting insoluble carrier particles carrying antibodies or antigens on the particle surfaces thereof with measurement objects, which are antigens or antibodies, to aggregate the insoluble carrier particles in an immunoreaction solution; and a measurement process measuring change in turbidity of the immunoreaction solution due to the aggregation reaction. The immunoturbidimetric assay of the present invention is not limited as long as it includes the aforementioned processes and uses the insoluble carrier particles of the present invention. For example, the immunoturbidimetric assay may be a latex immunoaggregation method.

In the immunoturbidimetric assay of the present invention, the measurement objects are not particularly limited, and examples thereof include the aforementioned antibodies or antigens.

In the immunoturbidimetric assay of the present invention, specimens containing the measurement object are not particularly limited and examples thereof include specimens common in laboratory tests. Examples of the specimens include biological samples such as whole blood, blood cells, serums, plasma, hemolysis samples, and urine.

In the present invention, for example, the specimens collected may be used directly as measurement samples. Alternatively, the specimens preliminarily applied with a dilution treatment, a filtration treatment, and a heating treatment in advance of an antigen-antibody reaction may be used as measurement samples. The solvent used in the dilution treatment is not particularly limited, and examples thereof include water, physiological saline, and a buffer solution.

The buffer of the buffer solution is applicable as long as it does not interfere with the reaction, and examples thereof include MES, phosphate, and Tris. For example, other components may be added to the buffer solution. For stabilizing reaction, bovine serum albumin (BSA) or the like may be added, for example.

In the dilution treatment, the dilution rate of the specimen is not particularly limited. For example, in the case where measurement is performed using the aforementioned specimen analyzing tools, the dilution rate can be set at lower degree.

In the aggregation reaction process, a method of immunoreacting insoluble carrier particles carrying antibodies or antigens on the particle surfaces thereof with the measurement objects (antigen-antibody reaction) is not particularly limited, and known methods can be used. For example, the reaction may be performed by adding a dispersion liquid, in which the insoluble carrier particle group is dispersed, to the measurement sample or by adding the measurement sample to the insoluble carrier particle group. In the former method, for example, the aforementioned measurement reagent is applicable. In the latter case, the insoluble carrier particle group may be the dispersion liquid or in a dried state. In the latter case, for example, the aforementioned specimen analyzing tools such as a test piece, a microchip, and a cartridge are applicable. Specifically, immunoreaction may be performed as follows: the insoluble carrier particle group in a dried state or in the state of dispersion liquid is placed to a reagent portion of a substrate, and then the measurement sample is added to the reagent portion.

The immunoreaction solution may contain, for example, the aforementioned buffer solutions, bovine serum albumin (BSA), and the like in addition to the insoluble carrier particles and the measurement objects.

The concentration of the insoluble carrier particle in the immunoreaction solution is not particularly limited, and is preferably in the range of 0.011 w/v % to 1 w/v %, more preferably in the range of 0.033 w/v % to 0.5 w/v %, and further preferably in the range of 0.055 w/v % to 0.3 w/v %. Further, with respect to the concentration of the insoluble carrier particle, the concentration of the group of smaller particles is preferably in the range of 0.01 w/v % to 0.5 w/v %, more preferably in the range of 0.03 w/v % to 0.3 w/v %, and further preferably in the range of 0.05 w/v % to 0.2 w/v %. Moreover, with respect to the concentration of the insoluble carrier particle, the concentration of the group of larger particles is preferably in the range of 0.001 w/v % to 0.05 w/v %, more preferably in the range of 0.003 w/v % to 0.04 w/v %, and further preferably in the range of 0.005 w/v % to 0.03 w/v %.

In the immunoreaction solution, the ratio between the particles of the smaller particle group and the particles of the larger particle group is not particularly limited. As a specific example, the weight ratio between the particles of the smaller particle group and the particles of the larger particle group is preferably in the range of 100:1 to 1:100, more preferably in the range of 10:1 to 1:10, and further preferably in the range of 5:1 to 1:5.

In the immunoturbidimetric assay of the present invention, the measurement process in which change in the turbidity of the immunoreaction solution is measured can be performed by measuring change in the absorbance of the immunoreaction solution.

Specific examples of the condition of the immunoreaction solution for detecting CRP by an immunoturbidimetric assay in the case where blood is used as specimens are as follows. However, the present invention is not limited thereto.

The concentration of the insoluble carrier particle in the immunoreaction solution is preferably in the range of 0.011 w/v % to 1 w/v %, more preferably in the range of 0.033 w/v % to 0.5 w/v %, and further preferably in the range of 0.055 w/v % to 0.3 w/v %, although it is not particularly limited. Further, with respect to the concentration of the insoluble carrier particle, the concentration of the group of smaller particles is preferably in the range of 0.01 w/v % to 0.5 w/v %, more preferably in the range of 0.03 w/v % to 0.3 w/v %, and further preferably in the range of 0.05 w/v % to 0.2 w/v %. Moreover, with respect to the concentration of the insoluble carrier particle, the concentration of the group of larger particles is preferably in the range of 0.001 w/v % to 0.05 w/v %, more preferably in the range of 0.003 w/v % to 0.04 w/v %, and further preferably in the range of 0.005 w/v % to 0.03 w/v %.

Subsequently, the change in the turbidity due to the aggregation reaction is measured. In other words, for example, the aggregation level of the insoluble carrier particle generated due to the immunoreaction is detected from change in the turbidity. Thereby, the quantitative determination of the measurement object can be performed indirectly.

The method of measuring the immunoreaction is not particularly limited, and an example thereof includes a method in which the absorbance and the scattering light of the immunoreaction solution after the immunoreaction are measured with optical means. For example, general-purpose optical measuring instruments can be used as the optical means. The method of evaluating measurement results also is not particularly limited. For example, the amount of change in absorbance within a certain period of time after the start of the immunoreaction may be used as an index. In this case, the certain period of time after the start of the immunoreaction is not particularly limited, and is preferably in the range of 0 to 5 minutes after the start of the immunoreaction, more preferably in the range of 30 to 180 seconds after the start of the immunoreaction, and further preferably in the range of 30 to 150 seconds after the start of the immunoreaction.

For example, the quantitative determination can be performed based on a calibration curve of standard samples containing measurement objects of known concentrations. Specifically, first, plural standard samples with concentrations set in a target concentration range are provided, the samples are immunoreacted under the same conditions, and the aggregation levels are detected from changes in turbidities. Then, the calibration curve is made from the known concentrations and the changes in the measurement values such as absorbance showing the turbidity, the measurement values of specimens are assigned to the calibration curve, and thereby the quantitative determination of the measurement objects in the specimens can be performed.

EXAMPLES

Next, Examples of the present invention are described together with Comparative Examples. However, the present invention is neither specified nor limited by the following Examples or Comparative Examples.

Example 1-1

In this example, a measurement reagent is prepared by the following method using lysine hydrochloride as an amino acid with a charged polar side chain.

A. Preparation of Insoluble Carrier Particle

Carboxylate modified polystyrene latex particles with the average particle sizes of 0.096 μm (10% solution (Seradyn Inc.)) were used as the smaller particles and carboxylate modified polystyrene latex particles with the average particle sizes of 0.213 μm (10% solution (Seradyn Inc.)) were used as the larger particles. First, the smaller particles were added to an activation solution of the composition shown in the following Table 1, reaction was performed at a room temperature (25° C.) for 1 hour, and functional groups on the surfaces of the smaller particles were activated. The activation solution was prepared as follows: to a 500 mmol/L MES buffer (pH 6.1), the composition other than the MES buffer was added, and then distilled water was added thereto so as to obtain the final concentrations shown in Table 1. The concentrations shown in the following composition are the final concentrations of each composition in the whole solution in which the smaller particles were mixed to the activation solution. The final concentration of the smaller particle in the whole solution was set at 1 w/v %. After the reaction, centrifugal separation (60000 rpm, 15 minutes) was performed to remove supernatant. Then, the smaller particles whose functional groups were activated were suspended in a 50 mmol/L MES buffer (pH 6.1), and sonicated to wash them. After performing the washing process again, centrifugal separation (60000 rpm, 15 minutes) was performed to remove supernatant. The smaller particles obtained were suspended in the MES buffer, and sonicated to obtain a latex solution (smaller particle). In this state, the concentration of the smaller particle in the latex solution (smaller particle) was 2 w/v %. Further, a latex solution (larger particle) was prepared in the same manner as the latex solution (smaller particle) except that the larger particles were used.

TABLE 1

(Composition of activation solution)

| Reagent | Final concentration |
| --- | --- |
| MES (pH 6.1 (Dojindo Laboratories)) | 50 mmol/L |
| NHS solution*[1] | 100 mmol/L |
| EDAC solution*[2] | 1.0 mmol/L |

*[1]NHS (N-hydroxysuccinimide (Nacalai Tesque, Inc.))

*[2]EDAC (1-ethyl-3-(3-dimethylaminopropyl)-carbodiimide hydrochloride (Sigma Chemical Co.))

Next, the latex solution (smaller particle) was mixed into a sensitization reaction solution for the smaller particles having the composition shown in the following Table 2, reaction was performed at a room temperature (25° C.) for 1 hour, and the smaller particles were sensitized with polyclonal antibodies and monoclonal antibodies. The sensitization reaction solution for the smaller particles was prepared as follows: to a 500 mmol/L MES buffer (pH 6.1), the composition other than the MES buffer was added, and then distilled water was added thereto so as to obtain the concentrations shown in Table 2. The concentrations of the composition shown in Table 2 are the final concentrations of each composition in the whole solution in which the latex solution (smaller particle) was mixed into the sensitization reaction solution for the smaller particles. The final concentration of the smaller particle in the whole solution was set at 1 w/v %. In the sensitization reaction solution for the smaller particles, the concentration ratio (weight ratio) between polyclonal antibodies and monoclonal antibodies, which were sensitized with the smaller particles, was 1:9.

TABLE 2

(Composition of sensitization reaction solution for smaller particles)

| Composition | Concentration |
| --- | --- |
| MES (pH 6.1 (Dojindo Laboratories)) | 50 mmol/L |
| BSA (Sigma Chemical Co.) | 1 mg/mL |
| Monoclonal antibody solution*[1] | 0.36 mg/mL |
| Polyclonal antibody solution*[2] | 0.04 mg/mL |

*[1]Rabbit-derived anti-human CRP monoclonal antibody solution (antibody concentration 10.5 mg/mL, clone No. 8 (Immuno Probe Co., Ltd.))

*[2]Rabbit-derived anti-human CRP polyclonal antibody solution (protein concentration 12.2 mg/mL (Oriental Yeast Co., Ltd.))

The smaller particles sensitized were suspended in a 50 mmol/L MES buffer (pH 6.1) after centrifugal separation (60000 rpm, 15 minutes), and then sonicated to wash them. Then, the centrifugal separation (60000 rpm, 15 minutes) was performed again to remove supernatant. Thereafter, the washed smaller particles were suspended in the MES buffer. The smaller particles suspended were mixed with a blocking buffer (50 mmol/L MES buffer (pH 6.1), 4 w/v % BSA) so that the concentration thereof became 1 w/v %. After sonicating the smaller particles, they were left to stand at 4° C. overnight, and then a blocking treatment was performed. After the blocking treatment, centrifugal separation (60000 rpm, 10 minutes) was performed to recover the smaller particles, and the smaller particles were dispersed using dispersion liquid having the composition shown in the following Table 3 so that the dispersion concentration of the smaller particle became 3.33 w/v %. In this manner, smaller particle dispersion liquid was prepared.

TABLE 3

(Composition of dispersion liquid)

| Composition | Concentration |
| --- | --- |
| Tris-HCl (pH 7.5 (Nacalai Tesque, Inc.)) | 50 mmol/L |
| BSA (Sigma Chemical Co.) | 2 w/v % |
| Saponin (Nacalai Tesque, Inc.) | 2.14 w/v % |
| Sucrose (Nacalai Tesque, Inc.) | 2 w/v % |
| Sodium azide (Nacalai Tesque, Inc.) | 0.1 w/v % |

The sensitization reaction of the larger particles was performed in the same manner as the smaller particles except that a sensitization reaction solution for the larger particles of the composition shown in the following Table 4 was used, the final concentration of the larger particle in the whole solution in which the larger particles were mixed to the sensitization reaction solution for the larger particles was set at 0.5 w/v %, and monoclonal antibodies were not added. Further, larger particle dispersion liquid was prepared by dispersing the larger particles in the dispersion liquid in the same manner as the smaller particles except that the dispersion concentration of the larger particle was set at 1.67 w/v %. In the sensitization reaction solution for the larger particles, the concentration ratio (weight ratio) between polyclonal antibodies and monoclonal antibodies, which were sensitized with the larger particles, was 10:0. The larger particle dispersion liquid was prepared as follows: to a 500 mmol/L MES buffer (pH 6.1), the composition other than the MES buffer was added, and then distilled water was added thereto so as to obtain the concentrations shown in Table 4. The concentrations of the composition shown in Table 4 are the final concentrations of each composition in the whole solution in which the latex solution (larger particle) was mixed into the sensitization reaction solution for the larger particles.

TABLE 4

(Composition of sensitization reaction solution for larger particles)

| Composition | Concentration |
| --- | --- |
| MES (pH 6.1 (Dojindo Laboratories)) | 50 mmol/L |
| BSA (Sigma Chemical Co.) | 1 mg/mL |
| Lysine hydrochloride | 0.5 mol/L |
| Polyclonal antibody solution* | 0.5 mg/mL |

*Rabbit-derived anti-human CRP polyclonal antibody solution (protein concentration 12.2 mg/mL (Oriental Yeast Co., Ltd.))

B. Preparation of Measurement Reagent

The smaller particle dispersion liquid and the larger particle dispersion liquid were mixed, and then the dispersion liquid was added to prepare a measurement reagent of this example. In the measurement reagent of this example, the concentration of the smaller particle was 0.517 w/v % and the concentration of the larger particle was 0.117 w/v %.

C. Visual Evaluation of Dispersibility

With respect to the larger particle dispersion liquid left to stand for 12 hours after the start of the blocking treatment, dispersibility was evaluated. The dispersibility was evaluated with three levels, namely, A, B, and C, as shown below.
A: Particles were dispersed without precipitation
B: Particles were partially dispersed
C: Particles were precipitated D. Instrumental Evaluation of Dispersibility The dispersibility of the measurement reagent of this example was evaluated using a general purpose automatic measuring instrument (product name "Bio-majesty (BM-8)" (Japan Electron Optics Laboratory Co. Ltd.)). First, a reagent diluent (2 w/v % BSA solution) and a reaction buffer (50 mmol/L Tris-HCl (pH 7.5), 1.28 w/v % NaCl (Nacalai Tesque, Inc.), and 0.05% BSA) were prepared. Then, after preparing the measurement reagent of this example, 21 μL of the measurement reagent of this example left to stand for a predetermined period of time (0, 24, and 48 hours) was added to a mixture of 6 μL of the reagent dilution and 63 μL of the reaction buffer. The mixture was stirred and the absorbance of the mixture at 658 nm was measured with time for 10 minutes from soon after the stirring using the measuring instrument. Then, with respect to the measurement reagent after being left to stand for the predetermined period of time, the rate of change (%) in the absorbance at the start of the measurement (soon after stirring) and the end of the measurement (10 minutes after stirring) was calculated with the following formula (1), and the dispersibility was evaluated.

$$\text{Rate of change (\%)} = [(a-b)/a] \times 100 \quad (1)$$

a=absorbance at start of measurement
b=absorbance at end of measurement

E. Measurement by Immunoturbidimetric Assay

The measurement of CRP by an immunoturbidimetric assay was performed as described below using the measurement reagent of this example. "C-Reactive Protein Antigen, High Pure" (Capricorn Products LLC.) was used as CRP.

That is, first, the CRP was diluted with a specimen diluent (50 mmol/L Tris-HCl (pH 7.5), 100 mmol/L NaCl (Nacalai Tesque, Inc.), 1 w/v % BSA) or CRP free serum (Oriental Yeast Co., Ltd.) to prepare CRP solutions (specimens) of predetermined concentrations (0, 0.1, 0.15, 1, 2.5, 5, 10, 20 mg/dL (mg/100 mL)). Then, the CRP solutions of the predetermined concentrations further were diluted 1.666-fold with the specimen diluents to prepare measurement samples.

63 μL of a reaction buffer (1.28 w/v % NaCl (Nacalai Tesque, Inc.)) and 21 μL of the measurement reagent of this example were added to 6 μL of the measurement sample to perform immunoreaction. After five minutes from the start of the reaction (addition), the absorbance of the immunoreaction solution at 658 nm was measured with a general purpose automatic measuring instrument (product name "Bio-majesty (BM-8)" (Japan Electron Optics Laboratory Co. Ltd.)). Then, the absorbance after 30 seconds from the start of the reaction was subtracted from the absorbance after 150 seconds from the start of the reaction, and the amount of change thereof was used in a measurement evaluation. With respect to the concentration of the latex particle in the immunoreaction solution, the concentration of the smaller particle was 0.121 w/v % and the concentration of the larger particle was 0.027 w/v %, and the concentration of the whole latex particle was 0.148 w/v %.

Example 1-2

The measurement reagent of this example was prepared in the same manner as Example 1-1 except that arginine hydrochloride of a concentration of 0.5 mol/L was used instead of lysine hydrochloride. Further, with respect to the measurement reagent of this example, the visual and instrumental evaluations of dispersibility were performed in the same manner as Example 1-1. Moreover, measurement by an immunoturbidimetric assay was performed in the same manner as Example 1-1 using the measurement reagent of this example.

Example 1-3

The measurement reagent of this example was prepared in the same manner as Example 1-1 except that histidine of a concentration of 0.5 mol/L was used instead of lysine hydrochloride. Further, with respect to the measurement reagent of this example, the visual and instrumental evaluations of dispersibility were performed in the same manner as Example 1-1. Moreover, measurement by an immunoturbidimetric assay was performed in the same manner as Example 1-1 using the measurement reagent of this example.

Example 1-4

The measurement reagent of this example was prepared in the same manner as Example 1-1 except that sodium aspartate of a concentration of 0.5 mol/L was used instead of lysine hydrochloride. Further, with respect to the measurement reagent of this example, the visual and instrumental evaluations of dispersibility were performed in the same manner as Example 1-1. Moreover, measurement by an immunoturbidimetric assay was performed in the same manner as Example 1-1 using the measurement reagent of this example.

Comparative Example 1-1

The measurement reagent of this example was prepared in the same manner as Example 1-1 except that lysine hydrochloride was not used. Further, with respect to the measurement reagent of this example, the visual and instrumental evaluations of dispersibility were performed in the same manner as Example 1-1. Moreover, measurement by an immunoturbidimetric assay was performed in the same manner as Example 1-1 using the measurement reagent of this example.

Comparative Example 1-2

The measurement reagent of this example was prepared in the same manner as Example 1-1 except that asparagine of a concentration of 0.5 mol/L was used instead of lysine hydrochloride. Further, with respect to the measurement reagent of this example, the visual and instrumental evaluations of dispersibility were performed in the same manner as Example 1-1. Moreover, measurement by an immunoturbidimetric assay was performed in the same manner as Example 1-1 using the measurement reagent of this example.

Comparative Example 1-3

The measurement reagent of this example was prepared in the same manner as Example 1-1 except that serine of a concentration of 0.5 mol/L was used instead of lysine hydrochloride. Further, with respect to the measurement reagent of this example, the visual and instrumental evaluations of dispersibility were performed in the same manner as Example 1-1. Moreover, measurement by an immunoturbidimetric assay was performed in the same manner as Example 1-1 using the measurement reagent of this example.

Comparative Example 1-4

The measurement reagent of this example was prepared in the same manner as Example 1-1 except that threonine of a concentration of 0.5 mol/L was used instead of lysine hydrochloride. Further, with respect to the measurement reagent of this example, the visual and instrumental evaluations of dispersibility were performed in the same manner as Example 1-1. Moreover, measurement by an immunoturbidimetric assay was performed in the same manner as Example 1-1 using the measurement reagent of this example.

The results of the visual comparison of the dispersibility with respect to the measurement reagents of Examples 1-1 to 1-4 are shown in the following Table 5. The results of the comparison of the dispersibility with respect to the measurement reagents of Comparative Examples 1-1 to 1-4 are shown in the following Table 6. As can be seen from Table 5, the dispersibility evaluations of the measurement reagents of Examples 1-1 to 1-4 were A and showed favorable dispersibility. In contrast, as can be seen from Table 6, the dispersibility evaluations of the measurement reagents of Comparative Examples 1-1 to 1-4 were C and showed inferior dispersibility.

TABLE 5

| Example | | Amino acid | Evaluation |
| --- | --- | --- | --- |
| Example 1-1 | 0.5 mol/L | Lysine hydrochloride | A |
| Example 1-2 | 0.5 mol/L | Arginine hydrochloride | A |
| Example 1-3 | 0.5 mol/L | Histidine | A |
| Example 1-4 | 0.5 mol/L | Sodium aspartate | A |

TABLE 6

| Comparative Example | | Amino acid | Evaluation |
| --- | --- | --- | --- |
| Comparative Example 1-1 | Not added | | C |
| Comparative Example 1-2 | 0.5 mol/L | Asparagine | C |
| Comparative Example 1-3 | 0.5 mol/L | Serine | C |
| Comparative Example 1-4 | 0.5 mol/L | Threonine | C |

Figure 2:
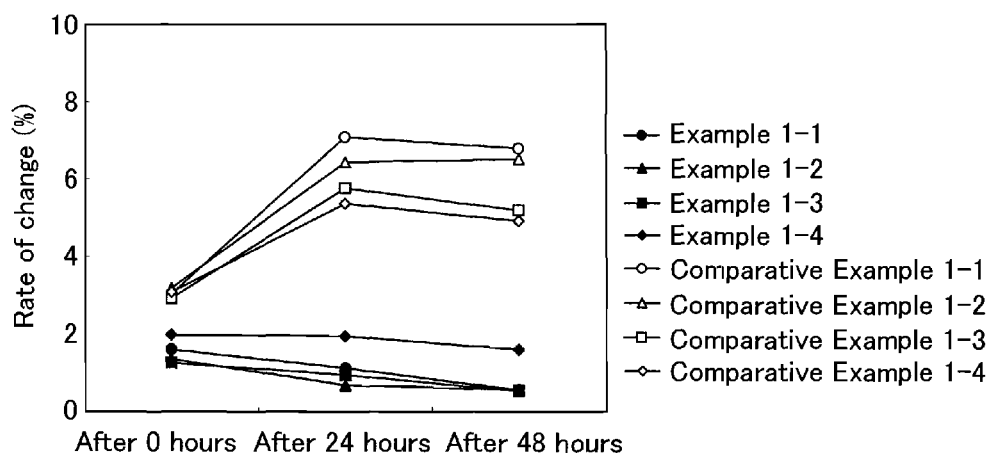
FIG. 2 is a graph showing the rate of change in the dispersibility before and after the measurement with respect to Example of the present invention and Comparative Example.

The results of the instrumental comparison of the dispersibility with respect to the measurement reagents of Examples 1-1 to 1-4 and the measurement reagents of Comparative Examples 1-1 to 1-4 are shown in FIGS. 1 and 2.

The results of the dispersibility with respect to the measurement reagents each left to stand for the predetermined period of time measured from the absorbance at the start of the measurement are shown in the graph in FIG. 1. In the graph in FIG. 1, a horizontal axis indicates the elapsed time after the preparation of the measurement reagent and a vertical axis indicates the absorbance at the start of the measurement. In the graph in FIG. 1, the plot of Example 1-1 is black circle, the plot of Example 1-2 is black triangle, the plot of Example 1-3 is black square, the plot of Example 1-4 is black rhombus, the plot of Comparative Example 1-1 is white circle, the plot of Comparative Example 1-2 is white triangle, the plot of Comparative Example 1-3 is white square, and the plot of Comparative Example 1-4 is white rhombus. In the graph in FIG. 1, the higher the absorbance is, the more the particles in the measurement reagents are aggregated. As can be seen from the graph in FIG. 1, with respect to the measurement reagents of Comparative Examples 1-1 to 1-4 the absorbance was increased with the time elapsed after the preparation of the measurement reagent, and it showed that the aggregation of the particles progressed. In contrast, with respect to the measurement reagents of Examples 1-1 to 1-4, changes in the absorbance with time elapsed after the preparation of the measurement reagents were small, and it showed that the dispersibility was retained.

The results of the dispersibility with respect to the measurement reagents each left to stand for the predetermined period of time measured from the rate of change in the absorbance before and after the start of the measurement are shown in the graph in FIG. 2. In the graph in FIG. 2, a horizontal axis indicates the elapsed time after the preparation of the measurement reagent and a vertical axis indicates the rate of change (%) in the absorbance. The plots in the graph in FIG. 2 are the same as those in the graph in FIG. 1. The measurement reagents were diluted with the reagent diluents or the like at the time of the measurement, and stirred with the measuring instrument. Therefore, with respect to the measurement reagent in which the particles were nonspecifically aggregated before the measurement, since the dispersion of the particles progresses during the measurement due to the dilution and stirring, the rate of change before and after the measurement was large. In contrast, with respect to the measurement reagent in which the particles were dispersed before the measurement, since the particles were already dispersed, the rate or change was small. As can be seen from the graph in FIG. 2, with respect to the measurement reagents of Comparative Examples 1-1 to 1-4, the rate of change was large in each predetermined time, and it showed that the particles in the measurement reagents were nonspecifically aggregated. Further, with respect to the measurement reagents of Comparative Examples 1-1 to 1-4, the rate of change was increased with time elapsed after the preparation of the measurement reagent, and it showed that the nonspecific aggregation of the particles in the measurement reagents progressed. In contrast, with respect to the measurement reagents of Examples 1-1 to 1-4, the rate of change was small at each predetermined time, and it showed that the particles in the measurement reagents were dispersed.

Figure 3:
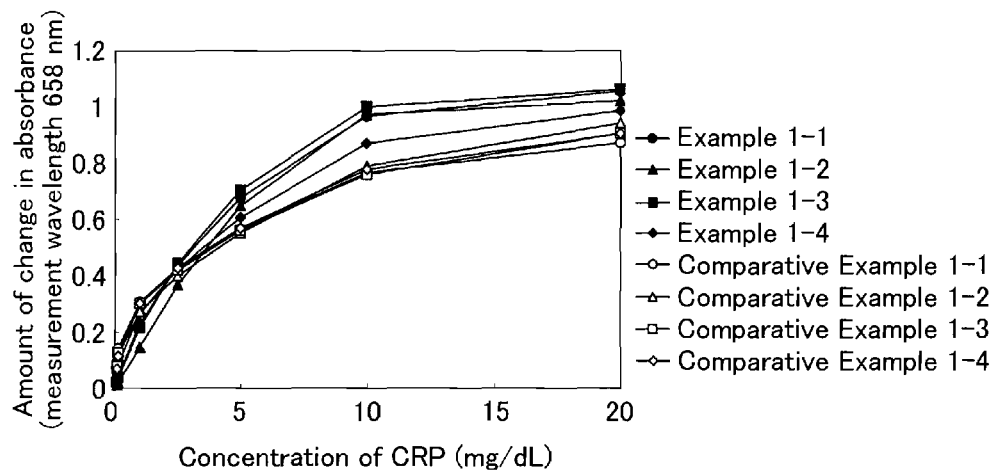
FIG. 3 is a graph showing measurement results of the immunoturbidimetric assay using Example of the present invention and Comparative Example.

The measurement results by the immunoturbidimetric assay with respect to the measurement reagents of Examples 1-1 to 1-4 and Comparative Examples 1-1 to 1-4 are shown in the graph in FIG. 3. In the graph in FIG. 3, a horizontal axis indicates the concentration of CRP used as the measurement sample (mg/dL (mg/100 mL)) and a vertical axis indicates the amount of change in the absorbance at each concentration. The plots in the graph in FIG. 3 are the same as those in the graph in FIG. 1. As can be seen from the graph in FIG. 3, as compared to the measurement reagents of Comparative Examples 1-1 to 1-4, the measurement reagents of Examples 1-1 to 1-4 retained the proportional relationship between increase in the concentration of CRP and increase in the absorbance in a wide range of CRP concentration, and showed higher measurement accuracy. Especially, in a moderate CRP concentration range of 5 to 10 mg/dL (5 to 10 mg/100 mL), sensitivity was increased.

Example 2-1

The measurement reagent of this example was prepared in the same manner as Example 1-1 except that the concentration of lysine hydrochloride was changed from 0.5 mol/L to 0.17 mol/L, the concentration of the smaller particle in the measurement reagent was set at 0.5 w/v %, the concentration of the larger particle in the measurement reagent was set at 0.1 w/v %, and the concentration of the whole latex particle was set at 0.6 w/v %.

Further, with respect to the measurement reagent of this example, the visual evaluation of dispersibility was performed in the same manner as Example 1-1 except that the measurement reagent left to stand for 24 hours was used.

Moreover, measurement by an immunoturbidimetric assay was performed in the same manner as Example 1-1 except that the measurement reagent of this example was used as the measurement reagent, and the concentration of the smaller particle was set at 0.117 w/v %, the concentration of the larger particle was set at 0.023 w/v %, and the concentration of the whole latex particle was set at 0.140 w/v % with respect to the concentration of the latex particle in the immunoreaction solution.

Example 2-2

The measurement reagent of this example was prepared in the same manner as Example 2-1 except that sodium glutamate of a concentration of 0.17 mol/L was used instead of lysine hydrochloride. Further, with respect to the measurement reagent of this example, the visual evaluation of dispersibility was performed in the same manner as Example 2-1. Moreover, measurement by an immunoturbidimetric assay was performed in the same manner as Example 2-1 using the measurement reagent of this example.

Example 2-3

The measurement reagent of this example was prepared in the same manner as Example 2-1 except that sodium aspartate of a concentration of 0.18 mol/L was used instead of lysine hydrochloride. Further, with respect to the measurement reagent of this example, the visual evaluation of dispersibility was performed in the same manner as Example 2-1. Moreover, measurement by an immunoturbidimetric assay was performed in the same manner as Example 2-1 using the measurement reagent of this example.

Comparative Example 2-1

The measurement reagent of this example was prepared in the same manner as Example 2-1 except that lysine hydrochloride was not used. Further, with respect to the measurement reagent of this example, the visual evaluation of dispersibility was performed in the same manner as Example 2-1. Moreover, measurement by an immunoturbidimetric assay was performed in the same manner as Example 2-1 using the measurement reagent of this example.

The results of the visual evaluation of the dispersibility with respect to the measurement reagents of Examples 2-1 to 2-3 are shown in the following Table 7. The result of the visual evaluation of the dispersibility with respect to the measurement reagent of Comparative Example 2-1 is shown in the following Table 8. As can be seen from Table 7, the dispersibility evaluation of the measurement reagent of Example 2-1 was A and the dispersibility evaluation of the measurement reagents of Examples 2-2 to 2-3 were B. In other words, the measurement reagents of Examples 2-1 to 2-3 showed favorable dispersibility. In contrast, as can be seen from Table 8, the dispersibility evaluation of the measurement reagent of Comparative Example 2-1 was C and it showed inferior dispersibility.

TABLE 7

| Example | | Amino acid | Evaluation |
|---|---|---|---|
| Example 2-1 | 0.17 mol/L | Lysine hydrochloride | A |
| Example 2-2 | 0.17 mol/L | Sodium glutamate | B |
| Example 2-3 | 0.18 mol/L | Sodium aspartate | B |

TABLE 8

| Comparative Example | Amino acid | Evaluation |
|---|---|---|
| Comparative Example 2-1 | Not added | C |

Figure 4:
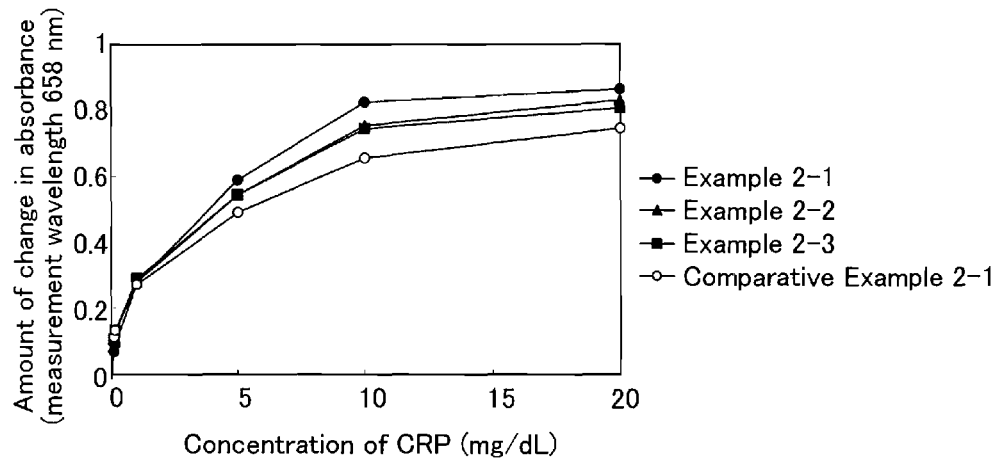
FIG. 4 is a graph showing measurement results of the immunoturbidimetric assay using still another Example of the present invention and still another Comparative Example.

The measurement results by the immunoturbidimetric assay with respect to the measurement reagents of Examples 2-1 to 2-3 and Comparative Example 2-1 are shown in the graph in FIG. 4. In the graph in FIG. 4, a horizontal axis indicates the concentration of CRP used as the measurement sample (mg/dL (mg/100 mL)) and a vertical axis indicates the amount of change in the absorbance at each concentration. In the graph in FIG. 4, the plot of Example 2-1 is black circle, the plot of Example 2-2 is black triangle, the plot of Example 2-3 is black square, and the plot of Comparative Example 2-1 is white circle. As can be seen from the graph in FIG. 4, as compared to the measurement reagent of Comparative Example 2-1, the measurement reagents of Examples 2-1 to 2-3 retained the proportional relationship between increase in the concentration of CRP and increase in the absorbance in a wide range of CRP concentration, and showed higher measurement accuracy.

Example 3-1

The measurement reagent of this example was prepared in the same manner as Example 1-1 except that sodium aspartate of a concentration of 0.075 mol/L was used instead of lysine hydrochloride, the concentration of the smaller particle in the measurement reagent was set at 0.533 w/v %, the concentration of the larger particle in the measurement reagent was set at 0.1 w/v %, and the concentration of the whole latex particle was set at 0.633 w/v %.

With respect to the measurement reagent of this example, the visual evaluation of dispersibility was performed in the same manner as Example 1-1.

Measurement by an immunoturbidimetric assay using the measurement reagent of this example was performed in the same manner as Example 1-1 except that the concentration of the smaller particle was set at 0.124 w/v %, the concentration of the larger particle was set at 0.023 w/v %, and the concentration of the whole latex particle was set at 0.148 w/v % with respect to the concentration of the latex particle in the immunoreaction solution, and the concentrations of the CRP solutions were set at 0, 0.1, 0.15, 1, 2.5, 5, 10 mg/dL (mg/100 mL).

Example 3-2

The measurement reagent of this example was prepared in the same manner as Example 3-1 except that the concentration of sodium aspartate was changed to 0.15 mol/L. Further, with respect to the measurement reagent of this example, the visual evaluation of dispersibility was performed in the same manner as Example 3-1. Moreover, measurement by an immunoturbidimetric assay was performed in the same manner as Example 3-1 using the measurement reagent of this example.

Example 3-3

The measurement reagent of this example was prepared in the same manner as Example 3-1 except that the concentration of sodium aspartate was changed to 0.6 mol/L. Further, with respect to the measurement reagent of this example, the visual evaluation of dispersibility was performed in the same manner as Example 3-1. Moreover, measurement by an immunoturbidimetric assay was performed in the same manner as Example 3-1 using the measurement reagent of this example.

Example 3-4

The measurement reagent of this example was prepared in the same manner as Example 3-1 except that the concentration of sodium aspartate was changed to 1.0 mol/L. Further, with respect to the measurement reagent of this example, the visual evaluation of dispersibility was performed in the same manner as Example 3-1. Moreover, measurement by an immunoturbidimetric assay was performed in the same manner as Example 3-1 using the measurement reagent of this example.

Example 3-5

The measurement reagent of this example was prepared in the same manner as Example 3-1 except that the concentration of sodium aspartate was changed to 2.0 mol/L. Further, with respect to the measurement reagent of this example, the visual evaluation of dispersibility was performed in the same manner as Example 3-1. Moreover, measurement by an immunoturbidimetric assay was performed in the same manner as Example 3-1 using the measurement reagent of this example.

Comparative Example 3-1

The measurement reagent of this example was prepared in the same manner as Example 3-1 except that sodium aspartate was not used. Further, with respect to the measurement reagent of this example, the visual evaluation of dispersibility was performed in the same manner as Example 3-1. Moreover, measurement by an immunoturbidimetric assay was performed in the same manner as Example 3-1 using the measurement reagent of this example.

The results of the visual evaluation of the dispersibility with respect to the measurement reagents of Examples 3-1 to 3-5 and Comparative Example 3-1 are shown in the following Table 9. As can be seen from Table 9, the dispersibility evaluation of the measurement reagent of Example 3-3 was A and the dispersibility evaluations of the measurement reagents of Examples 3-2 and 3-4 were B. In other words, the measurement reagents of Examples 3-2 to 3-4 showed favorable dispersibility.

TABLE 9

| Sodium aspartate concentration | | Evaluation |
| --- | --- | --- |
| 0 mol/L | (Comparative Example 3-1) | C |
| 0.075 mol/L | (Example 3-1) | C |
| 0.15 mol/L | (Example 3-2) | B |
| 0.6 mol/L | (Example 3-3) | A |
| 1.0 mol/L | (Example 3-4) | B |
| 2.0 mol/L | (Example 3-5) | C |

Figure 5:
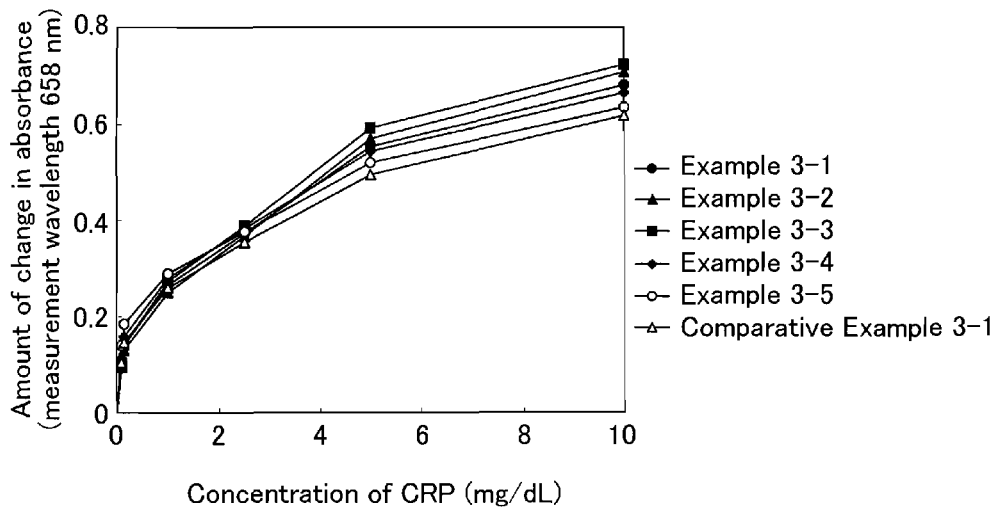
FIG. 5 is a graph showing measurement results of the immunoturbidimetric assay using yet another Example of the present invention and yet another Comparative Example.

The measurement results by the immunoturbidimetric assay with respect to the measurement reagents of Examples 3-1 to 3-5 and Comparative Example 3-1 are shown in the graph in FIG. 5. In the graph in FIG. 5, a horizontal axis indicates the concentration of CRP used as the measurement sample (mg/dL (mg/100 mL)) and a vertical axis indicates the amount of change in the absorbance at each concentration. In the graph in FIG. 5, the plot of Example 3-1 is black circle, the plot of Example 3-2 is black triangle, the plot of Example 3-3 is black square, the plot of Example 3-4 is black rhombus, the plot of Example 3-5 is white circle, and the plot of Comparative Example 3-1 is white triangle. As can be seen from the graph in FIG. 5, as compared to the measurement reagent of Comparative Example 3-1, the measurement reagents of Examples 3-1 to 3-5 retained the proportional relationship between increase in the concentration of CRP and increase in the absorbance in a wide range of CRP concentration, and showed higher measurement accuracy. As described above, the measurement reagents of Examples 3-1 to 3-5 in which antibodies are brought into contact with latex particles in the presence of the amino acid with a charged polar side chain can be measured in a wide range of measurement concentration, and showed higher measurement accuracy. Further, the measurement reagents of Examples 3-2 to 3-4 containing the amino acid with a charged polar side chain at the concentration of 0.15 mol/L to 1 mol/L in the sensitization reaction solution showed superior suppression of nonspecific aggregation.

Example 4-1

The measurement reagent of this example was prepared in the same manner as Example 1-1 except that the smaller particles were not used and only the larger particles were used as the insoluble carrier particle group, the concentration of the larger particle in the measurement reagent was set at 0.167 w/v % and the concentration of the whole latex particle was set at 0.167 w/v %.

With respect to the measurement reagent of this example, the instrumental evaluation of dispersibility was performed in the same manner as Example 1-1.

Measurement by an immunoturbidimetric assay was performed in the same manner as Example 1-1 except that the measurement reagent of this example was used as the measurement reagent, the concentration of the smaller particle was set at 0 w/v %, the concentration of the larger particle was set at 0.039 w/v %, and the concentration of the whole latex particle was set at 0.039 w/v % with respect to the concentration of the latex particle in the immunoreaction solution, the concentrations of the CRP were set at 0, 0.1, 0.15, 1, 2.5, 5 mg/dL (mg/100 mL), and the dilution rate of the CRP solutions was set at 6.66-fold.

Example 4-2

The measurement reagent of this example was prepared in the same manner as Example 4-1 except that arginine hydrochloride of a concentration of 0.5 mol/L was used instead of lysine hydrochloride. Further, the instrumental evaluation of dispersibility and the measurement by an immunoturbidimetric assay were performed in the same manner as Example 4-1 using the measurement reagent of this example.

Example 4-3

The measurement reagent of this example was prepared in the same manner as Example 4-1 except that histidine of a concentration of 0.5 mol/L was used instead of lysine hydrochloride. Further, the instrumental evaluation of dispersibility and the measurement by an immunoturbidimetric assay were performed in the same manner as Example 4-1 using the measurement reagent of this example.

Example 4-4

The measurement reagent of this example was prepared in the same manner as Example 4-1 except that sodium aspartate of a concentration of 0.5 mol/L was used instead of lysine hydrochloride. Further, the instrumental evaluation of dispersibility was performed in the same manner as Example 4-1 using the measurement reagent of this example.

Comparative Example 4-1

The measurement reagent of this example was prepared in the same manner as Example 4-1 except that lysine hydrochloride was not used. Further, the instrumental evaluation of dispersibility and the measurement by an immunoturbidimetric assay were performed in the same manner as Example 4-1 using the measurement reagent of this example.

Comparative Example 4-2

The measurement reagent of this example was prepared in the same manner as Example 4-1 except that asparagine of a concentration of 0.5 mol/L was used instead of lysine hydrochloride. Further, the instrumental evaluation of dispersibility was performed in the same manner as Example 4-1 using the measurement reagent of this example.

Comparative Example 4-3

The measurement reagent of this example was prepared in the same manner as Example 4-1 except that serine of a concentration of 0.5 mol/L was used instead of lysine hydrochloride. Further, the instrumental evaluation of dispersibility and the measurement by an immunoturbidimetric assay were performed in the same manner as Example 4-1 using the measurement reagent of this example.

Comparative Example 4-4

The measurement reagent of this example was prepared in the same manner as Example 4-1 except that threonine of a concentration of 0.5 mol/L was used instead of lysine hydrochloride. Further, the instrumental evaluation of dispersibility was performed in the same manner as Example 4-1 using the measurement reagent of this example.

Figure 6:
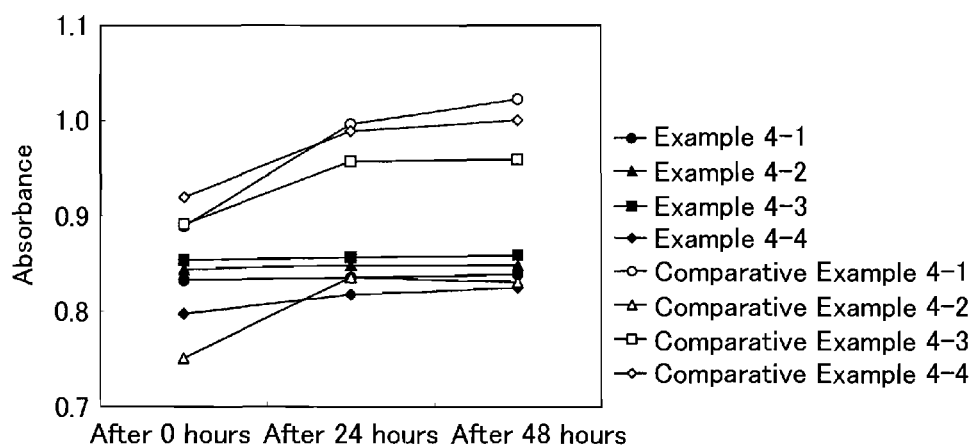
FIG. 6 is a graph showing measurement results of the dispersibility with respect to yet another Example of the present invention and yet another Comparative Example.
Figure 7:
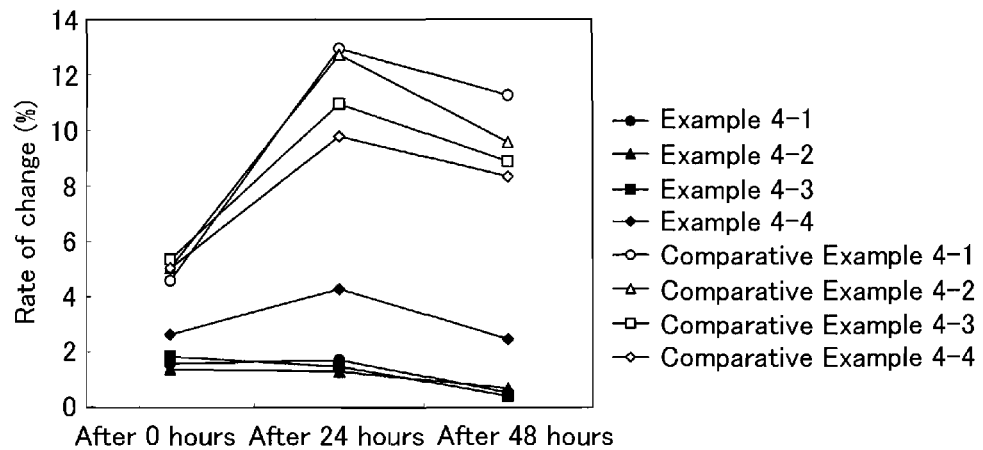
FIG. 7 is a graph showing the rate of change in the dispersibility before and after the measurement with respect to yet another Example of the present invention and yet another Comparative Example.

The results of the instrumental evaluation of the dispersibility with respect to the measurement reagents of Examples 4-1 to 4-4 and Comparative Examples 4-1 to 4-4 are shown in FIGS. 6 and 7.

The absorbance at the start of the measurement at each predetermined time is shown in the graph in FIG. 6. In the graph in FIG. 6, a horizontal axis indicates the elapsed time after the preparation of the measurement reagent and a vertical axis indicates the absorbance at the start of the measurement. In the graph in FIG. 6, the plot of Example 4-1 is black circle, the plot of Example 4-2 is black triangle, the plot of Example 4-3 is black square, the plot of Example 4-4 is black rhombus, the plot of Comparative Example 4-1 is white circle, the plot of Comparative Example 4-2 is white triangle, the plot of Comparative Example 4-3 is white square, and the plot of Comparative Example 4-4 is white rhombus. In the graph in FIG. 6, the higher the absorbance is, the more the particles in the measurement reagents are nonspecifically aggregated. As can be seen from the graph in FIG. 6, with respect to the measurement reagents of Comparative Examples 4-1 to 4-4, the absorbance was increased with time elapsed after the preparation, and the nonspecific aggregation of the particles in the measurement reagents were progressed. In contrast, with respect to the measurement reagents of Examples 4-1 to 4-4, the absorbance was low soon after the preparation of the measurement reagent (0 hour), and the particles in the measurement reagents were dispersed. Further, with respect to the measurement reagents of Examples 4-1 to 4-4, changes in the absorbance with time elapsed after the preparation were small, and it showed that the dispersibility was retained.

The rate of change in the absorbance before and after the measurement at the predetermined time is shown in the graph in FIG. 7. In the graph in FIG. 7, a horizontal axis indicates the elapsed time after the preparation of the measurement reagent and a vertical axis indicates the rate of change (%) in the absorbance. The plots in the graph in FIG. 7 are the same as those in the graph in FIG. 6. As described above, the rate of change is increased when the particles in the measurement reagent are aggregated, and the rate of change is decreased when the particles in the measurement reagent are dispersed. As can be seen from the graph in FIG. 7, with respect to the measurement reagents of Comparative Examples 4-1 to 4-4, the rate of change was large at each predetermined time, and the particles in the measurement reagents were nonspecifically aggregated. Further, with respect to the measurement reagents of Comparative Examples 4-1 to 4-4, the rate of change was increased with time elapsed after the preparation, and it showed that the aggregation of the particles in the measurement reagents was progressed. In contrast, with respect to the measurement reagents of Examples 4-1 to 4-4, the rate of change was small at each predetermined time, and it showed that the particles in the measurement reagents were dispersed.

Figure 8:
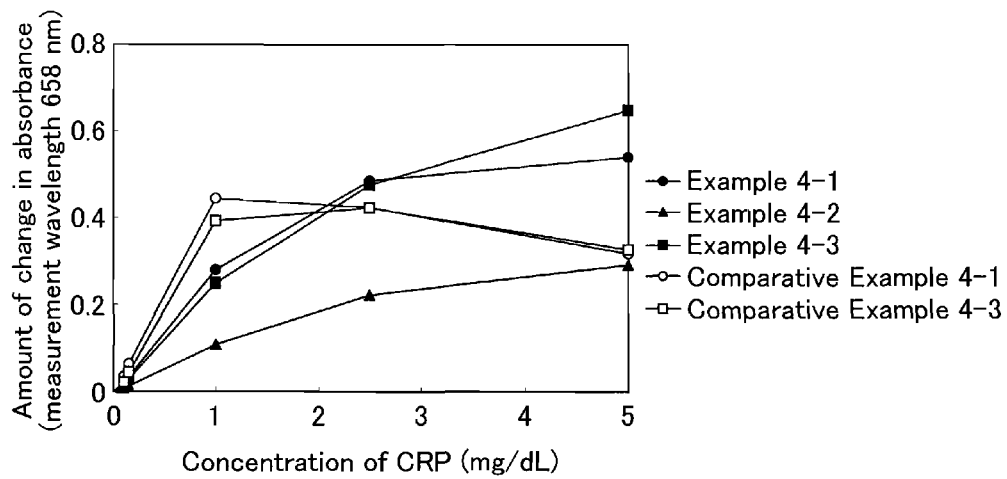
FIG. 8 is a graph showing measurement results of the immunoturbidimetric assay using yet another Example of the present invention and yet another Comparative Example.

The measurement results by the immunoturbidimetric assay with respect to the measurement reagents of Examples 4-1 to 4-3 and Comparative Examples 4-1 and 4-3 are shown in the graph in FIG. 8. In the graph in FIG. 8, a horizontal axis indicates the concentration of CRP used as the measurement sample (mg/dL (mg/100 mL)) and a vertical axis indicates the amount of change in the absorbance at each concentration. The plots in the graph in FIG. 8 are the same as those in the graphs in FIGS. 6 and 7 except that there are no plots of Example 4-4 and Comparative Examples 4-2 and 4-4. As can be seen from FIG. 8, as compared to the measurement reagents of Comparative Example 4-1 and 4-3, the measurement reagents of Examples 4-1 to 4-3 retained the proportional relationship between increase in the concentration of CRP and increase in the absorbance in a wide range of CRP concentration, and showed higher measurement accuracy.

INDUSTRIAL APPLICABILITY

A method of producing insoluble carrier particles, insoluble carrier particles, a measurement reagent, a specimen analyzing tool, an immunoturbidimetric assay, and an immunochromatograph method of the present invention can be used in laboratory tests, various screenings, and the like. The intended uses thereof are not limited and they are applicable to a wide range of fields such as medical science, pharmaceutical science, and biochemistry.

The invention claimed is:

1. A method of producing an insoluble carrier particle carrying an antibody or an antigen on a particle surface thereof, comprising the following sensitization reaction process (A):
   (A) bringing the antibody or the antigen into contact with the insoluble carrier particle in the presence of an amino acid with a charged polar side chain in a sensitization reaction solution, wherein a concentration of the amino acid with a charged polar side chain in the sensitization reaction solution is greater than 0.1 mol/L and is equal to or less than 1 mol/L.

2. The method of producing an insoluble carrier particle according to claim 1, wherein the amino acid with a charged polar side chain is a basic amino acid or an acidic amino acid.

3. The method of producing an insoluble carrier particle according to claim 1, wherein in the sensitization reaction process (A), the insoluble carrier particle is a latex particle.

4. The method of producing an insoluble carrier particle according to claim 3, wherein in the sensitization reaction process (A), the latex particle is a latex particle for chemical bonding.

5. An insoluble carrier particle used in an immunoturbidimetric assay, wherein the insoluble carrier particle is produced by the method of producing an insoluble carrier particle according to claim 1.

6. A measurement reagent used in an immunoturbidimetric assay, wherein the measurement reagent contains the insoluble carrier particle according to claim 5.

7. The measurement reagent according to claim 6, wherein
   the measurement reagent contains an insoluble carrier particle group including a plurality of insoluble carrier particles,
   the insoluble carrier particle group includes two types of insoluble carrier particle groups having different average particle sizes, and
   at least one of the two types of insoluble carrier particle groups is an insoluble carrier particle group including a plurality of insoluble carrier particles according to claim 5.

8. The measurement reagent according to claim 7, wherein an insoluble carrier particle group having a larger average particle size out of the two types of insoluble carrier particle groups is an insoluble carrier particle group including a plurality of insoluble carrier particles according to claim 5.

9. The measurement reagent according to claim 6, wherein an average particle size of the insoluble carrier particle according to claim 5 is in a range of 0.03 to 2.0 μm.

10. The measurement reagent according to claim 6, wherein an average particle size of the insoluble carrier particle according to claim 5 is in a range of 0.08 to 2.0 μm.

11. The measurement reagent according to claim 6, wherein an average particle size of the insoluble carrier particle according to claim 5 is in a range of 0.12 to 0.5 μm.

12. A specimen analyzing tool, containing the measurement reagent according to claim 6.

13. The specimen analyzing tool according to claim 12, wherein the specimen analyzing tool is any one of a test piece, a cartridge, and a microchip.

14. An immunoturbidimetric assay, comprising:
    an aggregation reaction process immunoreacting insoluble carrier particles carrying antibodies or antigens on particle surfaces thereof with measurement objects, which are antigens or an antibodies, to aggregate the insoluble carrier particles in an immunoreaction solution; and
    a measurement process measuring change in turbidity of the immunoreaction solution due to the aggregation reaction, wherein the insoluble carrier particle according to claim 5 is used as the insoluble carrier particle.

15. The immunoturbidimetric assay according to claim 14, wherein in the aggregation reaction process,
    an insoluble carrier particle group including a plurality of insoluble carrier particles is used, and wherein
    the insoluble carrier particle group includes two types of insoluble carrier particle groups having different average particle sizes, and
    at least one of the two types of insoluble carrier particle groups is an insoluble carrier particle group including a plurality of insoluble carrier particles according to claim 5.

16. The immunoturbidimetric assay according to claim 15, wherein an insoluble carrier particle group having a larger average particle size out of the two types of insoluble carrier particle groups is an insoluble carrier particle group including a plurality of insoluble carrier particles according to claim 5.

17. The immunoturbidimetric assay according to claim 14, wherein an average particle size of the insoluble carrier particle according to claim 5 is in a range of 0.03 to 2.0 μm.

18. The immunoturbidimetric assay according to claim 14, wherein an average particle size of the insoluble carrier particle according to claim 5 is in a range of 0.08 to 2.0 μm.

19. The immunoturbidimetric assay according to claim 14, wherein an average particle size of the insoluble carrier particle according to claim 5 is in a range of 0.12 to 0.5 μm.

* * * * *